US012733829B2

(12) United States Patent
Lai et al.

(10) Patent No.: US 12,733,829 B2
(45) Date of Patent: Sep. 15, 2026

(54) SYSTEM AND METHOD FOR TISSUE ANALYSIS USING REMOTE PPG

(71) Applicant: KONINKLIJKE PHILIPS N.V., Eindhoven (NL)

(72) Inventors: Marco ' Lai, Eindhoven (NL); Bernardus Hendrikus Wilhelmus Hendriks, Eindhoven (NL); Gerhardus Wilhelmus Lucassen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 99 days.

(21) Appl. No.: 18/837,915

(22) PCT Filed: Feb. 15, 2023

(86) PCT No.: PCT/EP2023/053772
§ 371 (c)(1),
(2) Date: Aug. 13, 2024

(87) PCT Pub. No.: WO2023/156466
PCT Pub. Date: Aug. 24, 2023

(65) Prior Publication Data

US 2025/0148591 A1 May 8, 2025

(30) Foreign Application Priority Data

Feb. 18, 2022 (EP) .................................... 22157397
Feb. 18, 2022 (EP) .................................... 22157408
Jan. 29, 2023 (WO) ................ PCT/EP2023/052103

(51) Int. Cl.
*A61B 5/026* (2006.01)
*A61B 5/00* (2006.01)

(52) U.S. Cl.
CPC .......... *A61B 5/0261* (2013.01); *A61B 5/0075* (2013.01); *A61B 5/7264* (2013.01)

(58) Field of Classification Search
CPC .............. A61B 5/0075; A61B 5/02416; A61B 5/02433; A61B 5/026; A61B 5/0261; A61B 5/0295; A61B 5/7264; A61B 5/72
See application file for complete search history.

(56) References Cited

U.S. PATENT DOCUMENTS 12,220,214 B2 * 2/2025 Hsiung ............. A61B 5/02416
2010/0312128 A1 12/2010 Karst
2014/0213910 A1 7/2014 Durkin
(Continued)

FOREIGN PATENT DOCUMENTS

WO 2015023990 A1 2/2015

OTHER PUBLICATIONS

International Search Report and Written Opinion of PCT/EP2023/053772, dated Apr. 23, 2023.
(Continued)

*Primary Examiner* — Carolyn A Pehlke

(57) ABSTRACT

A tissue analysis system and method process hyperspectral images to classify tissue types within the images. A presence or level of tissue oxygenation is estimated for each tissue type as well as a PPG perfusion. The estimated tissue oxygenation and PPG perfusion information are combined to provide a tissue status for each tissue type. The system and method uses remote PPG sensing.

15 Claims, 6 Drawing Sheets

(56) References Cited

U.S. PATENT DOCUMENTS

| | | | | |
|---|---|---|---|---|
| 2014/0221845 | A1* | 8/2014 | Mestha | A61B 5/7282 600/479 |
| 2016/0106328 | A1* | 4/2016 | Mestha | A61B 5/7253 600/479 |
| 2017/0055894 | A1 | 3/2017 | Panasyuk | |
| 2020/0138360 | A1 | 5/2020 | Fan | |
| 2020/0294228 | A1 | 9/2020 | Hu | |
| 2020/0342587 | A1 | 10/2020 | Epperlein | |
| 2021/0065372 | A1 | 3/2021 | Zhuk | |
| 2022/0354418 | A1 | 11/2022 | Bourquin | |
| 2024/0041342 | A1 | 2/2024 | Lai | |
| 2024/0148289 | A1* | 5/2024 | Wang | G06T 7/0012 |

OTHER PUBLICATIONS

Zaunseder, Sebastian et al."Spatio-Tempoal Analysis of Blood Perfusin by Imaging Photoplethysmography", Optical Diagnostics and Sensing XVIII, Proc. of SPIE, vol. 10501, 2018.

Lai, Marco et al "Perfusion Monitoring by Contactless Photoplethysmography Imaging", IEEE 16TH International Symposium on Biomedical Imaging, Apr. 2019.

Lai, Marco et al "Perfusion Monitoring by Non-Contact Photoplethysmorgraphic (PPG) Imaging", R-TN-2016/00448, 2017.

Lai, Marco et al "Evaluation of a Non-contact Photo-Plethysmographic Imaging (iPPG) System for Peripheral Arterial Disease Assessment", SPIE Medical Imaging, 2021.

Lai, Marco et al "Automated Classification of Brain Tissue: Comparison between Hyperspectral Imaging and Diffuse Reflectance Spectroscopy". SPIE Medical Imaging, 2020.

Lu, Guolan et al "Medical Hyperspectral Imaging: A Review", Journal of Biomedical Optics, vol. 19, No. 1, Jan. 2014.

Fodor, Margot et al, "Hyperspectral Imaging and Machine Perfusion in Solid Organ Transplantation: Clinical Potentials of Combining Two Novel Technologies", Journal of Clinical Medicine, 2021.

Stratonnikov, AA et al, Evaluation of Blood Oxygen Saturation in vivo from Diffuse Reflectance Spectra, Journal of Biomedical Opticals, vol. 6, No. 4, pp. 457-467, 2001.

* cited by examiner

SYSTEM AND METHOD FOR TISSUE ANALYSIS USING REMOTE PPG

CROSS-REFERENCE TO PRIOR APPLICATIONS

This application is the U.S. National Phase application under 35 U.S.C. § 371 of International Application No. PCT/EP2023/053772, filed on Feb. 15, 2023, which claims the benefit of European Patent Application No. 22157397.5, filed on Feb. 18, 2022 and European Patent Application No. 22157408.0, filed on Feb. 18, 2022 and International Application No. PCT/EP2023/052103, filed on Jan. 29, 2023. These applications are hereby incorporated by reference herein.

FIELD OF THE INVENTION

This invention relates to the analysis of tissue using photoplethysmography (PPG) analysis.

BACKGROUND OF THE INVENTION

Microcirculation is the circulation of the blood in the smallest blood vessels, present in the vasculature embedded within organ tissues. The structure of the microvasculature is extremely complex, as so many capillaries are present in the tissues, with the individual capillaries so convoluted that the blood flow at any given point in any given capillary could be in any direction. For this reason, it can be stated that their overall function becomes averaged. That is, there is an average rate of blood flow through each tissue capillary bed, an average capillary pressure within the capillaries, and an average rate of transfer of substances between the blood of the capillaries and the surrounding interstitial fluid. This is the perfusion of the tissue.

Organ perfusion is a crucial indicator of injury and disease, which may include inflammation, stagnant or stopped blood flow, and all pathologies that can lead to global tissue hypoxia and organ dysfunction. Perfusion monitoring can be used to assess these microvascular injuries and many others, such as the progress of healing of either burned skin or wounds or the recovery of the perfusion downstream of a vessel lesion, and the necrosis (e.g., foot ulceration, sepsis) for patients with diabetes.

Non-contact PPG imaging is a recent emerging technology able of monitoring skin perfusion. PPG imaging utilizes an off-the-shelf camera and a light source to remotely detect the dynamic changes in blood volume beneath the skin and allows extracting blood pulsation signals. PPG imaging allows for the elaboration of large tissue areas, thus building a so-called perfusion map, which is a great advantage with respect to contact PPG. PPG imaging has shown to be capable of detecting skin perfusion perturbations, such as irritation, temperature changes and even flow blockage during pressure measurements and has even been evaluated for peripheral arterial disease assessment.

It is possible to build an amplitude map, that represents the amplitude of the PPG signal per image sensing pixel. Furthermore, it is also possible to build a delay map, which provides a measure of the average time delay between the PPG signal wave of each pixel and a reference PPG signal. There is a small delay in the blood pulsation arrival, due to small differences in the microcirculatory bad, such as the resistance and elasticity of the vessels, as well as different artery branches that supply the recorded tissues.

For the purposes of this application, which relates to processing of non-contact PPG signals, perfusion may be defined as the amplitude of a PPG signal of the tissue, namely the amplitude of the pulsatility extracted from the tissue.

It is well known that the perfusion level is not the same everywhere in the body. For example, in a study by the applicant, PPG imaging of the hands and feet were studied, and it was found that the perfusion level is higher on the palms of the hands rather than on the sole of the feet. This is also true for organs, such as the intestine. The small intestine and the colon have different functions, are far away and are supplied by different artery branches, and accordingly have different perfusion levels.

If different tissue types are present in a single image of a remote PPG camera, a general PPG image analysis will average these differences. For example, if an anastomosis is being performed (e.g. after removal of part of the intestine) and the level of perfusion is measured via PPG imaging, there are different intestines in the image. The image analysis will also not show whether the perfusion difference is physiological or due to a lesion (e.g. ischemia, inflammation).

For example, during open bowel resection, a part of the colon or small intestine is surgically removed to remove a tumor. First, a surgeon mobilizes the bowel from the surrounding organs and membranes. The bowel is clamped on both sides of the tumor and blood flow towards that part is interrupted. The surgeon will then cut out the diseased part of the bowel and stitch the two clamped sides back together, which is called the anastomosis. The intestinal anastomosis is to establish communication between two formerly distant portions of the intestine. This procedure restores intestinal continuity after removal of the pathological condition affecting the bowel. If the anastomosis does not properly heal due to inadequate perfusion, leakages occur. Leakages are dangerous and can lead to severe infections and require hospitalization and reoperation. These leakages occur in 5 to 10% of patients undergoing bowel resection. Here, objective perfusion parameters could help identify inadequate healing.

In particular, it would be desirable to be able to measure the perfusion separately in the two parts of the anastomosis, since the perfusion levels are not expected to be the same due to the anatomical differences between the different tissue types.

Another measure of interest for determining tissue or organ health is the level of tissue oxygenation.

It would therefore be of interest to be able to monitor perfusion and oxygenation of different tissue types separately to provide a more complete assessment of tissue status information.

US 2020/138360 discloses the use of multispectral imaging for measuring oxygenation. It also discloses the use of PPG and oxygenation to provide tissue classification.

Zaunseder, Sebastian et. al., "Spatio-temporal analysis of blood perfusion by imaging photoplethysmography", Progress in Biomedical Optics and Imaging, SPIE-Int. Soc. for Optical Engineering vol. 10501, 20 Feb. 2018 (XP060099995) discloses a method of analyzing blood perfusion using remote PPG. A perfusion speed index is calculated for every pixel point of the PPG delay map. The distribution of all the indices give an indication on the perfusion.

SUMMARY OF THE INVENTION

The invention is defined by the claims.

According to examples in accordance with an aspect of the invention, there is provided a system for tissue analysis, comprising:

- a processor adapted to receive hyperspectral images captured by a hyperspectral image sensor and to process the hyperspectral images to:
- classify tissue types and segment the hyperspectral images into one or more regions corresponding to different tissue types;
- estimate a presence or level of tissue oxygenation for each tissue type;
- derive a PPG perfusion map from PPG amplitude levels at one or more wavelengths of the hyperspectral image sensor; and
- combine the estimated tissue oxygenation and PPG perfusion information from the PPG perfusion map to derive a tissue perfusion and oxygenation status for each tissue type.

This system makes use of remote PPG sensing to derive a PPG perfusion map from PPG amplitude levels. A hyperspectral image sensor is used so that different images contain different spectral content.

By imaging with different spectral content, tissue oxygenation levels can be determined. The oxygenation level may be a binary indication (oxygenated or not oxygenated) or it may be a level of oxygenation.

The hyperspectral images also enable different tissue types to be identified, such as tissues of different organs or different regions of an organ. This image segmentation may be performed from only one wavelength image or it may use multiple wavelength images. For each separate tissue type, the oxygenation information as well as the PPG perfusion information is combined to provide a tissue status which takes both into account.

The oxygenation is for example obtained from an analysis of multiple wavelengths. Different tissue types may have different perfusion as well as different oxygenation at homeostasis, so by separating images into different tissue types and treating them separately, more accurate information is obtained. By using hyperspectral imaging to first classify tissue types (e.g. an organ) the classification information can be used to determine a standard level of perfusion at homeostasis. This helps in better assessing whether that specific tissue is well perfused or not. Only after the first step of classification are the oxygenation levels extracted.

The processor may be adapted to classify the tissue types using a machine learning algorithm. This performs image based segmentation and classification.

The tissue types for example comprise tissues for different organ types or tissues for different regions of an organ.

The hyperspectral images for example comprise a set of 2D images, each at a different wavelength of a set of wavelengths.

The processor is for example adapted to estimate the tissue oxygenation using spectral information from hyperspectral images for at least two different wavelengths and to derive the PPG perfusion map from at least one of the 2D images. Various approaches are known for extracting blood oxygen saturation from diffuse reflectance spectra and from hyperspectral cameras.

The processor may be further adapted to derive a PPG delay map from PPG relative delays between different image regions.

The PPG delay map is obtained from relative delays of arrival of the pulsatile blood flow to the tissue. The delay information is for different image regions, i.e. the image data associated with different pixels of the image sensor.

The PPG delay map may be used as part of the classification of tissue types. For example, different tissue regions may have different delay times. Thus, the delay information may also assist the tissue classification. For example, a first tissue region may have delay times in a first range which is non-overlapping with delay times in a second range of a second tissue type. Each range may be considered to be an average value plus or minus a number (e.g. 1) of standard deviations (i.e. a statistical range rather than a range which includes all values).

Thus, different tissue regions have distinct delay characteristics. This may arise because the different tissue types are supplied by different arteries and hence have a different path and hence path length to the heart. This may arise in the case of different portions of the intestines, and these portions may become adjacent during open bowel resection. There is a resulting intestinal anastomosis with communication between formerly distant portions of the intestine.

The relative delays for example comprise a delay relative to a reference PPG signal which is an average delay time period for all image regions for a frame of image data. The delay is computed as the average time delay between the PPG signal wave of each pixel and the reference PPG signal, over a certain time period.

The length of the time period includes at least a heartbeat cycle and the reference PPG signal is obtained as a spatial average of the all pixel values of a video (or series of images) which is a time-dependent signal modulated at the heart rate. A signal is created which varies over time, frame by frame.

The tissue perfusion and oxygenation status for example comprises one of:

- above normal pulsation and normal oxygenation;
- above normal pulsation and below normal oxygenation;
- normal pulsation and normal oxygenation;
- normal pulsation and below normal oxygenation;
- below normal pulsation and normal oxygenation;
- below normal pulsation and below normal oxygenation.

Thus, a tissue status may be obtained which considers both the perfusion and the level of oxygenation.

The system for example also comprises the hyperspectral image sensor for capturing the hyperspectral images.

The invention also provides a computer-implemented tissue analysis method, comprising:

- receiving hyperspectral image sensor images;
- classifying tissue types and segmenting the hyperspectral images into one or more regions corresponding to different tissue types;
- estimating a presence or level of tissue oxygenation for each tissue type;
- deriving a PPG perfusion map from PPG amplitude levels at one or more wavelengths of the hyperspectral image sensor; and
- combining the estimated tissue oxygenation and PPG perfusion information from the PPG perfusion map to derive a tissue perfusion and oxygenation status for each tissue type.

Classifying the tissue types is preferably performed using a machine learning algorithm.

The tissue types for example comprise tissues for different organ types or tissues for different regions of an organ.

The hyperspectral images preferably comprise a set of 2D images, each at a different wavelength of a set of wavelength and wherein the method comprises:

estimating the tissue oxygenation using spectral information from hyperspectral images for at least two different wavelengths; and deriving the PPG perfusion map from at least one of the 2D images.

The method may further comprise deriving a PPG delay map from PPG relative delays between different image sensor regions. The PPG delay map may be used for the classification of the tissue types.

The invention also provides a computer program comprising computer program code means which is adapted, when said program is run on a computer, to implement the method defined above. The invention also provides a processor which is programed with the computer program.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
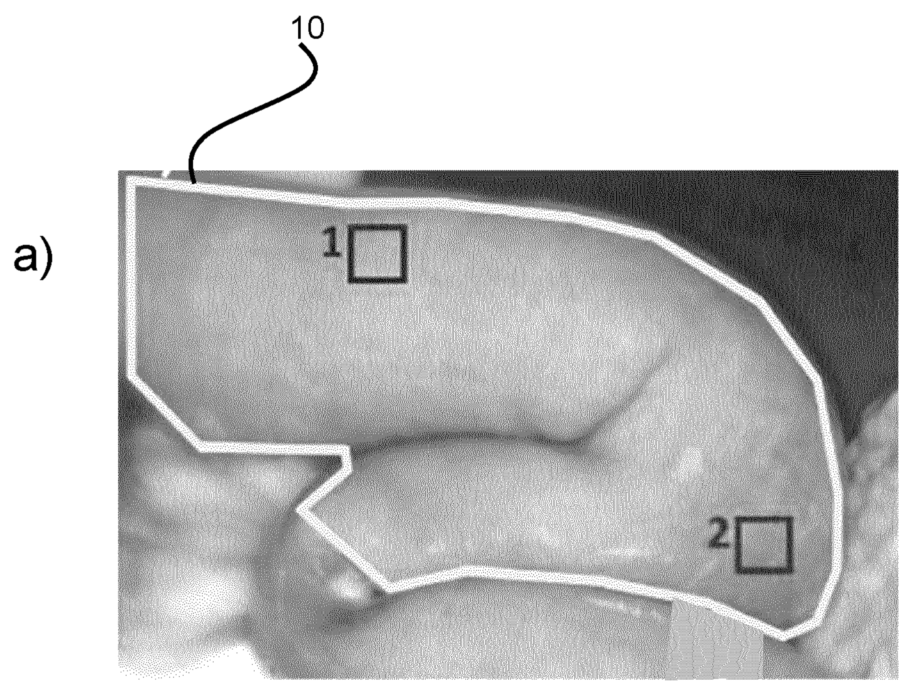
FIG. 1 shows a representation of a frame of a video acquired of the intestine and a global PPG signal derived from the video.
Figure 1:
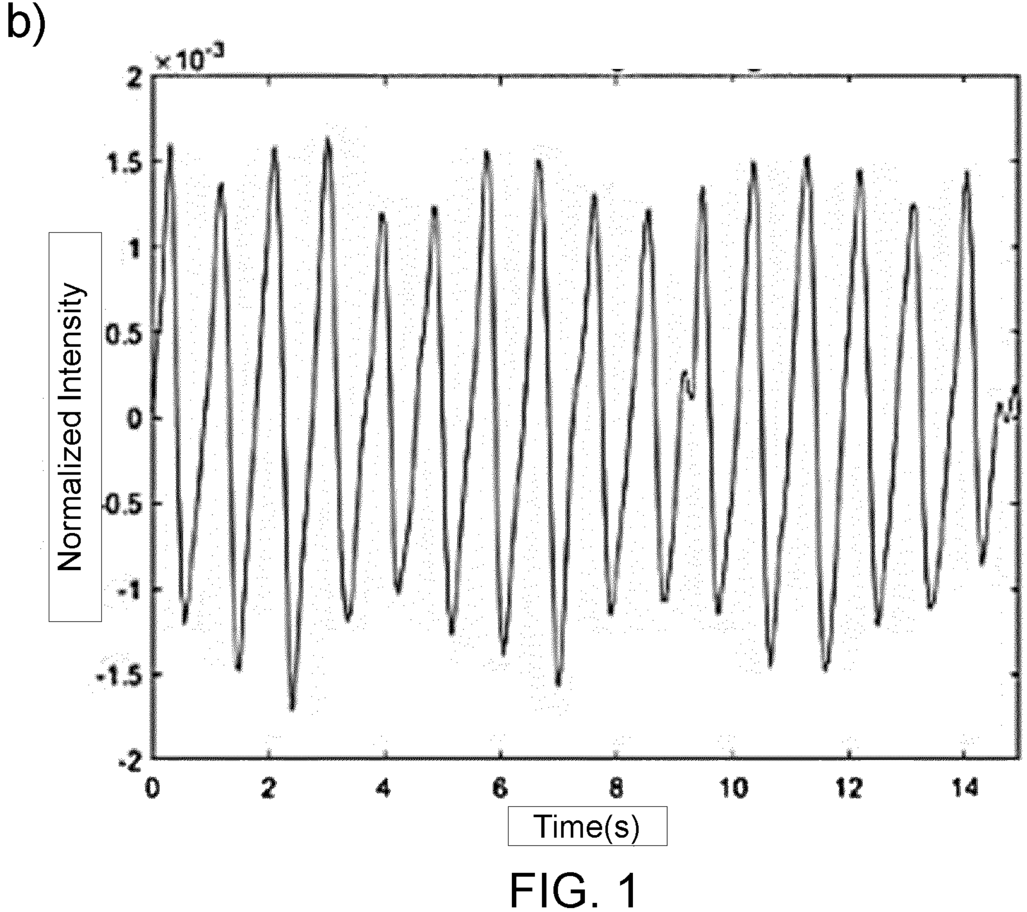

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a tissue analysis system and method which process hyperspectral images to classify tissue types within the images. A presence or level of tissue oxygenation is estimated for each tissue type as well as a PPG perfusion. The estimated tissue oxygenation and PPG perfusion information are combined to provide a tissue status for each tissue type. The system and method uses remote PPG sensing.

Before describing the system and method of the invention, the known operation of a remote PPG imaging system, and the known image processing methods, will first be described.

Remote PPG imaging enables a determination of tissue perfusion from images captured of the tissue of interest, e.g. the skin or even tissue beneath the skin. Remote PPG typically uses ambient light, functioning as broad band white light source, and the diffuse and specular reflections are analyzed for different color components. Remote PPG imaging may be used to construct a PPG amplitude map and a PPG delay map.

For this purpose, a camera or a series of cameras (at one or multiple wavelengths) captures video of the tissue area, e.g. skin, at a distance. The measurements derived from the video are remote PPG images, which provide non-contact measurement of a pulse signal by analyzing subtle changes of skin color (or organ color) i.e. at different wavelengths of the light.

It has been proposed to use remote PPG for inflammation detection. It has also been proposed in European Patent Application No. 20214955.5 to measure perfusion based both on a PPG amplitude level and also information about the distribution of the PPG phases, such as a standard deviation or interquartile range of a phase map.

By extracting pulse signals at each individual location of the skin region (corresponding to each pixel of the cameras) a spatial map of the pulse signal can be derived, showing both amplitude and delay. This perfusion map thus represents the amplitude and delay of the PPG signal per pixel and hence per location of the skin.

FIG. 1 (*a*) shows a representation of a frame of a video acquired of the intestine. By spatial averaging the pixel values in the region of interest (ROI) 10, a signal can be derived from the video, modulated at the heart rate. This signal is shown in FIG. 1 (*b*) as a normalized intensity of the PPG signal versus time.

The PPG signal of FIG. 1 (*b*) represents an average for the whole region of interest.

However, separate signals may also be captured from smaller regions of interest, shown as region 1 and region 2 in FIG. 1 (*a*).

Figure 2:
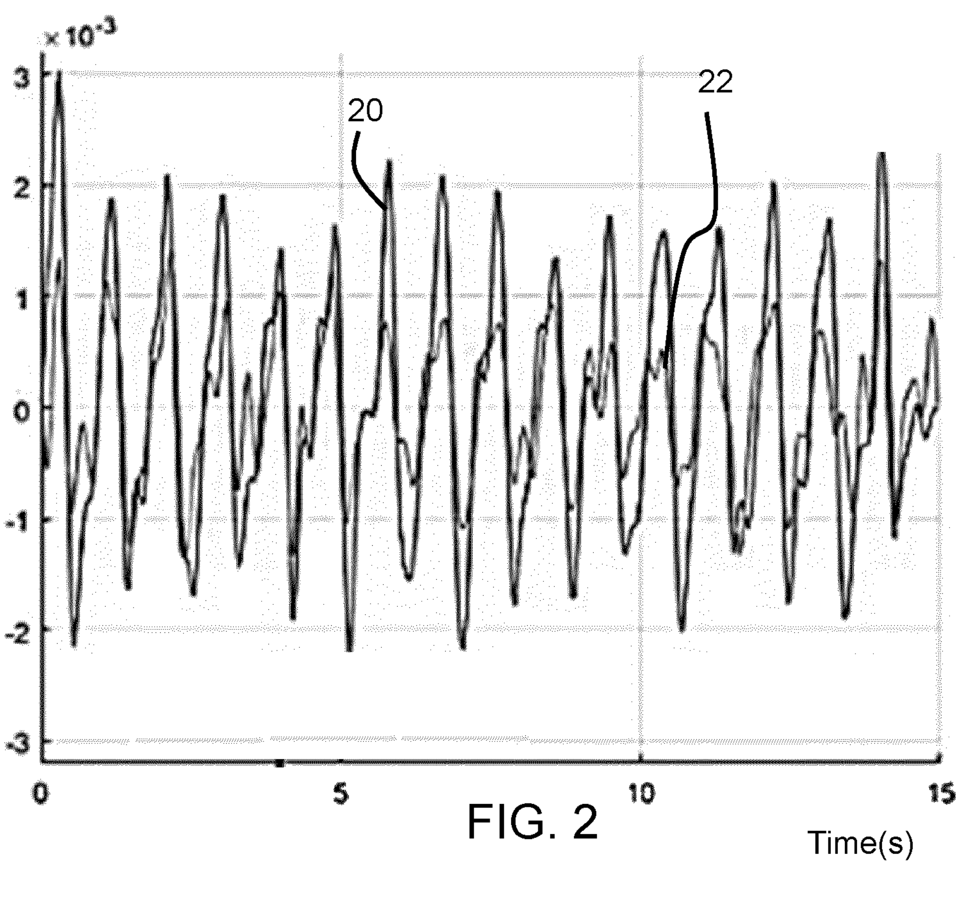
FIG. 2 shows separate PPG signals for separate regions of interest.

FIG. 2 shows separate PPG signals, as a first signal 20 for the first region of interest and a second signal 22 for the second region of interest. The two PPG signals are modulated at the same heart rate frequency, but show a different amplitude. By extracting the amplitude from the PPG signal of each separate region of tissue, i.e. from each corresponding pixel of the captured video, a PPG perfusion map may be obtained, as shown in FIG. 3.

Figure 3:
FIG. 3 shows a PPG perfusion map.

FIG. 3 is a black and white representation. However, the PPG perfusion may be color-coded, for example assigning a more red color to areas with higher perfusion and a more blue color to areas with lower perfusion. The PPG amplitude map thus represents the amplitude of the PPG signal per pixel and hence per location of the skin or other tissue being analyzed.

Additional valuable information may be obtained by analyzing the PPG signals.

Figure 4:
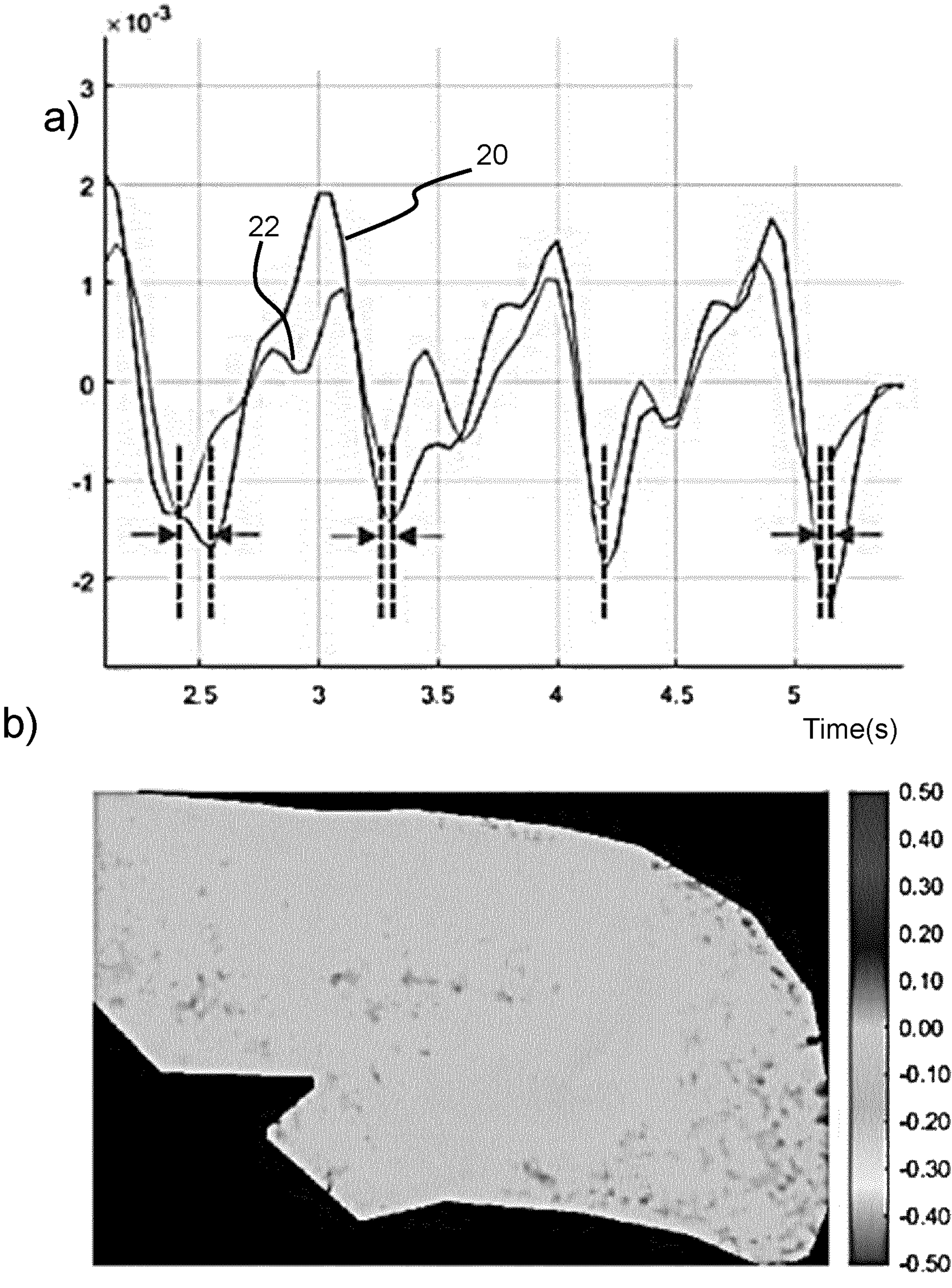
FIG. 4 shows a zoom-in of the PPG signals extracted from the two regions of interest from FIG. 2 and a PPG delay map.

FIG. 4 (*a*) shows a zoom-in of the PPG signals extracted from the two regions of interest from FIG. 2. Even though the signals are extracted simultaneously from the same organ, the pulsation arrives slightly before in one area than in the other. There is a small delay in the blood pulsation arrival, due to small differences in the microcirculatory bed, such as the resistance and elasticity of the vessels, as well as different artery branches that supply the recorded tissues.

The delays of the PPG signals of each pixel with respect to a reference signal may be extracted and used for building a delay map. The delay map is shown in FIG. 4.

Since the delay between the signals is not always constant but varies during the acquisition, an average delay is used between signals per pixel.

The average delay represents the average time delay between the PPG signal of each pixel and a reference PPG signal. In this way a signal in time is built. The length of the PPG signal should include at least a heartbeat cycle, so it is subject dependent.

The average delay is a value of delay assigned to each pixel. From the plot of FIG. 4, it can be seen that there is a difference in time arrival between the peaks of the PPG signals. Therefore, for each pixel, the average of these delay (with respect to a reference signal) is assigned. At the end, the delay map is built, where each pixel contains the average delay between the PPG signal of that pixel and the reference PPG signal.

By acquiring a video stream, a series of images is obtained over time, for example with a frame rate of 20 frames per second. In order to compute the global PPG signal over time, the pixel values of the frame 1 are spatially averaged, so that the 2D set of pixels yields one value. The pixels of frame 2 are then averaged, and so on.

Eventually, a PPG signal is obtained over time (with the same length as the video that has been acquired), where each value of the signal is a spatial average of one corresponding frame of the video acquired. The image frames for example comprise 968×728 pixels, by way of example.

The PPG signal of each pixel is thus compared with the global PPG signal being used as a reference. The value assigned to each pixel "n" of the delay map thus represents the average delay between the PPG signal in the pixel "n" and the global PPG signal being used as a reference. Thus, the value of the delay for each pixel in the PPG delay map represents the average delay (in terms of average time shift) between the PPG signal of that pixel and the global PPG signal. The delays are for example computed by using the lock-in amplification algorithm.

The delay map thereby provides a measure of the average time delay between the PPG signal wave of each pixel and the reference PPG signal for at least one heartbeat cycle. The reference PPG signal is the global PPG signal of FIG. 1 (*b*) extracted from the entire region on interest of the intestine.

Since the reference signal is extracted from the entire region of interest, a PPG signal from a given location of the image is likely to be in phase with the reference.

Similar to the map of the amplitude, FIG. 4 (*b*) is a black and white representation. However, the PPG delay map may be color-coded. The Hue, Saturation, Value (HSV) color system is for example employed, since it works well with the periodicity of the PPG signal.

For extracting the amplitude maps and delay maps, a lock-in amplification method may be used.

Details on how to calculate the PPG maps using the lock-in amplification method can be found in:

(i) Lai M, Shan C, Ciuhu-Pijlman C, Izamis M L. Perfusion monitoring by contactless photoplethysmography imaging, 2019 IEEE 16th International Symposium on Biomedical Imaging (ISBI 2019) 2019 Apr. 8 (pp. 1778-1782). IEEE; and (ii) Lai M, Dicorato C S, de Wild M, Verbakel F, Shulepov S, Groen J, Notten M, Lucassen G, van Sambeek M R, Hendriks B H. Evaluation of a non-contact Photo-Plethysmographic Imaging (iPPG) system for peripheral arterial disease assessment, Medical Imaging 2021: Biomedical Applications in Molecular, Structural, and Functional Imaging 2021 Feb. 15 (Vol. 11600, p. 116000F). International Society for Optics and Photonics.

Because of the great advantages that the remote PPG technology has shown for remotely and non-invasively assessing skin-level perfusion, PPG imaging can be translated to organ perfusion assessment for detecting the perfusion of the microvasculature tissue bed beneath the organ surface, without any modification to the current acquisition setup.

Remote PPG sensing may be performed using a standard image sensor, which receives reflected ambient light.

However, there is also the option of using hyperspectral imaging. Hyperspectral imaging (HSI) is an emerging imaging modality for medical applications that offers great potential for non-invasive disease diagnosis and surgical guidance. The objective of hyperspectral imaging is to collect a three-dimensional dataset of spatial and spectral information, known as hypercube.

Figure 5:
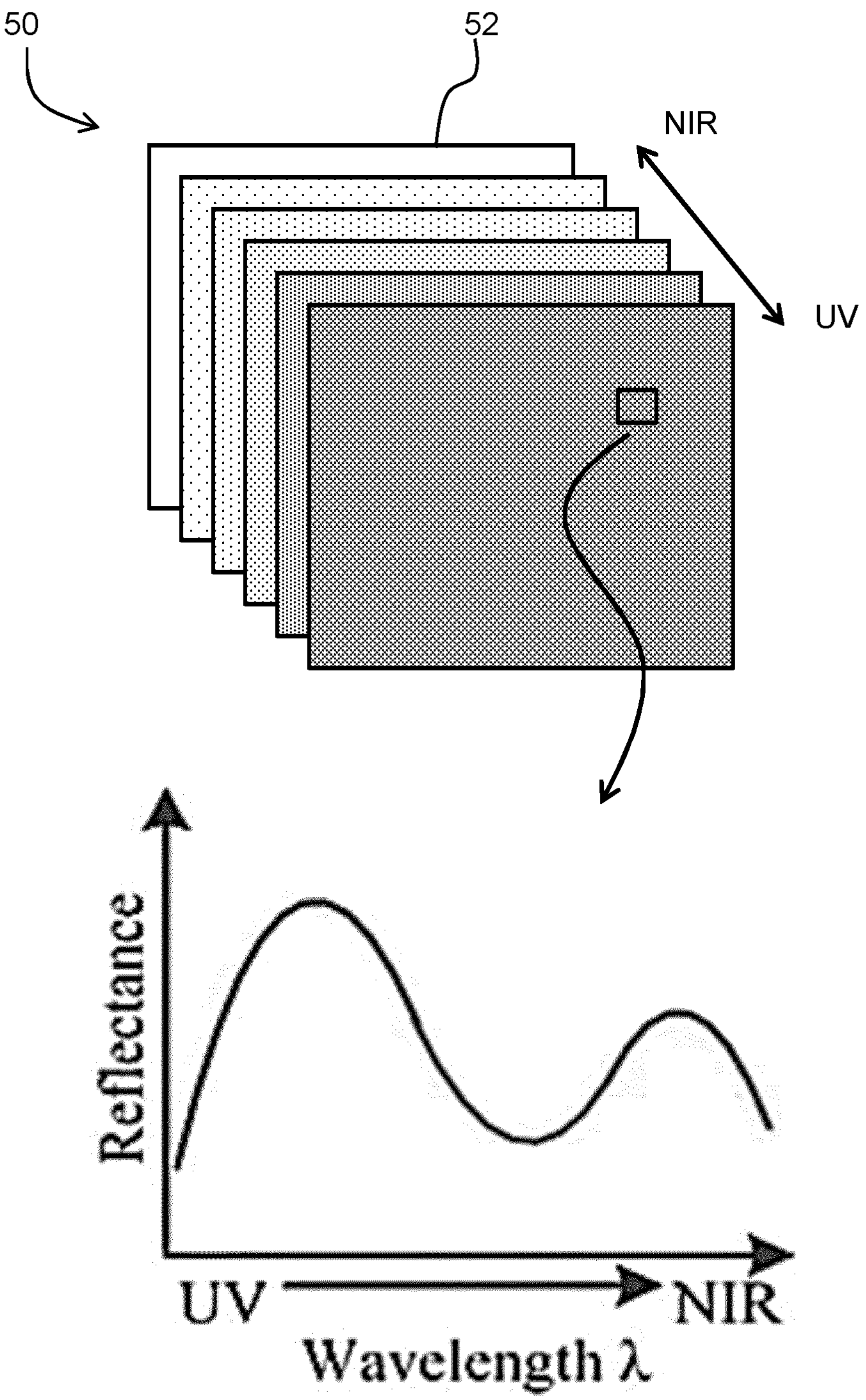
FIG. 5 shows a hypercube of a hyperspectral camera.

As shown in FIG. 5, the hypercube is three-dimensional dataset 50 comprising two-dimensional images 52 at each of a set of wavelengths. FIG. 5 also shows a reflectance curve (i.e. the spectral signature) of a pixel in each image.

This invention makes use of hyperspectral imaging so that the tissue in the field of view can be classified and the different tissue types can be segmented, such as the different organs in the abdominal area.

The advantages of hyperspectral imaging will now be explained. A conventional RGB camera has a sensor sensitive to a red bell-shaped wavelength range, to a green range and to a blue. The spectral signature of an object cannot be identified, since there are only 3 points (1 for red, 1 for green and 1 for blue), which are not even specific to any individual wavelength. HSI allows multiple images to be acquired at once of the same object, where each image represents a narrow wavelength range of the electromagnetic spectrum, i.e. a narrow spectral band. HSI camera can acquire several spectral bands, not only in the visible range but also in the UV and IR range. For example, HIS sensors are known which acquire 25 bands in the IR range, and which acquire 16 bands in the visible range. There are also HIS sensors with many more bands.

Because of the large number of wavelengths, the spectral signature of the tissue recorded can be extracted, and the tissue can be identified and classified. The classification based on the spectral signature of the tissue can be much more precise with HSI than with an RGB image.

Tissue oxygenation can be computed by combining in a model several wavelengths of interest, acquired with the HSI camera. RGB cameras have red, green, and blue channel sensitive to much broader WL ranges, so extracting oxygenation from a normal RGB camera is not possible. The use of an HSI camera enables tissue classification, tissue oxygen levels to be determined and PPG maps to be processed. The HIS camera for example has at least 10 spectral bands, for example at least 20 spectral bands.

A presence or level of tissue oxygenation can thus be determined for each tissue type as well as measuring PPG amplitude levels separately for the different tissue types. The perfusion measurement only needs one wavelength of the hyperspectral images, although perfusion may be determined using multiple wavelengths. The estimated tissue oxygenation and PPG perfusion information from the PPG perfusion are then combined to derive a tissue perfusion and oxygenation status for each tissue type.

Figure 6:
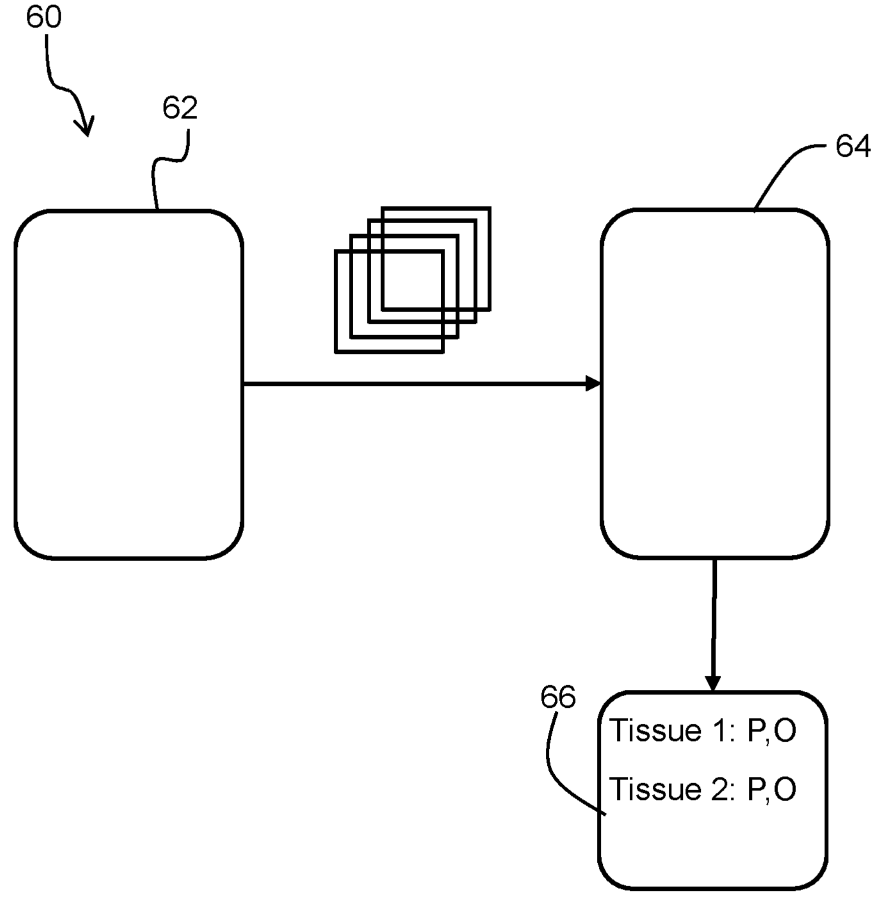
FIG. 6 shows system for tissue analysis.

FIG. 6 shows a system 60 for tissue analysis. The system comprises one or more hyperspectral imaging cameras 62 and a processor 64 adapted to receive the hyperspectral images and process the images.

The image processing classifies tissue types, e.g. Tissue 1 and Tissue 2, and segments the hyperspectral images into one or more regions corresponding to different tissue types. A presence or level of tissue oxygenation is estimated for each tissue type and PPG amplitude levels are obtained for each tissue type from a PPG perfusion map (at one or multiple wavelengths of the hyperspectral camera). The estimated tissue oxygenation and PPG perfusion information are combined to derive a tissue perfusion and oxygenation status for each tissue type.

This information is for example output by a display 66, which may provide PPG maps (amplitude maps and/or delay maps) or as PPG signals over time.

The tissue classification for example uses machine learning algorithms, such as Support Vector Machines (SVMs) and Convolutional Neural Networks (CNNs).

The field of view of the hyperspectral camera could include all of the organs inside the abdomen or only a part of the organs inside. By classifying the different organs present in the field of view, a comparison is of perfusion is prevented between different organs, which can have different levels of perfusion due to their different functions and they can even be supplied by different artery branches. A standard level of perfusion at homeostasis may be obtained for each classified tissue type, for comparison with a derived tissue perfusion status.

The oxygenation analysis gives an indication of the amount of oxygen in the tissue, whereas the PPG imaging extracts perfusion of the tissue in terms of blood pulsatility. This is an indication of the blood that flows inside the organ.

Oxygenation and perfusion (PPG pulsatility) are combined in order to give a better indication of the status of the organs tissue, for example by avoiding necrosis. As shown in FIG. 6, the system outputs perfusion and oxygenation information ("P,O") for the different tissue types. The information is displayed graphically as explained above, and FIG. 6 is thus a simplified representation of the system functionality.

The combination of oxygenation and perfusion enables six potential situations to be identified:

- (i) High (above normal) pulsation and oxygenation: this condition may indicate tissue inflammation/irritation, with a normal level of oxygenation
- (ii) High pulsation and no oxygenation: this condition may indicate tissue inflammation/irritation, but the level of oxygen is very low (hypoxia).
- (iii) Normal pulsation and oxygenation: this is the normal status of a heathy organ.
- (iv) Normal pulsation and no oxygenation: the heart is pumping the blood in organ, but the level of oxygen is very low (hypoxia).
- (v) No pulsation and oxygenation: the heart is not pumping the blood in the organ, but the level of oxygen is still god enough.
- (vi) No pulsation and no oxygenation: this is the worst condition, in which the blood flow is blocked and the level of oxygen is low.

Figure 7:
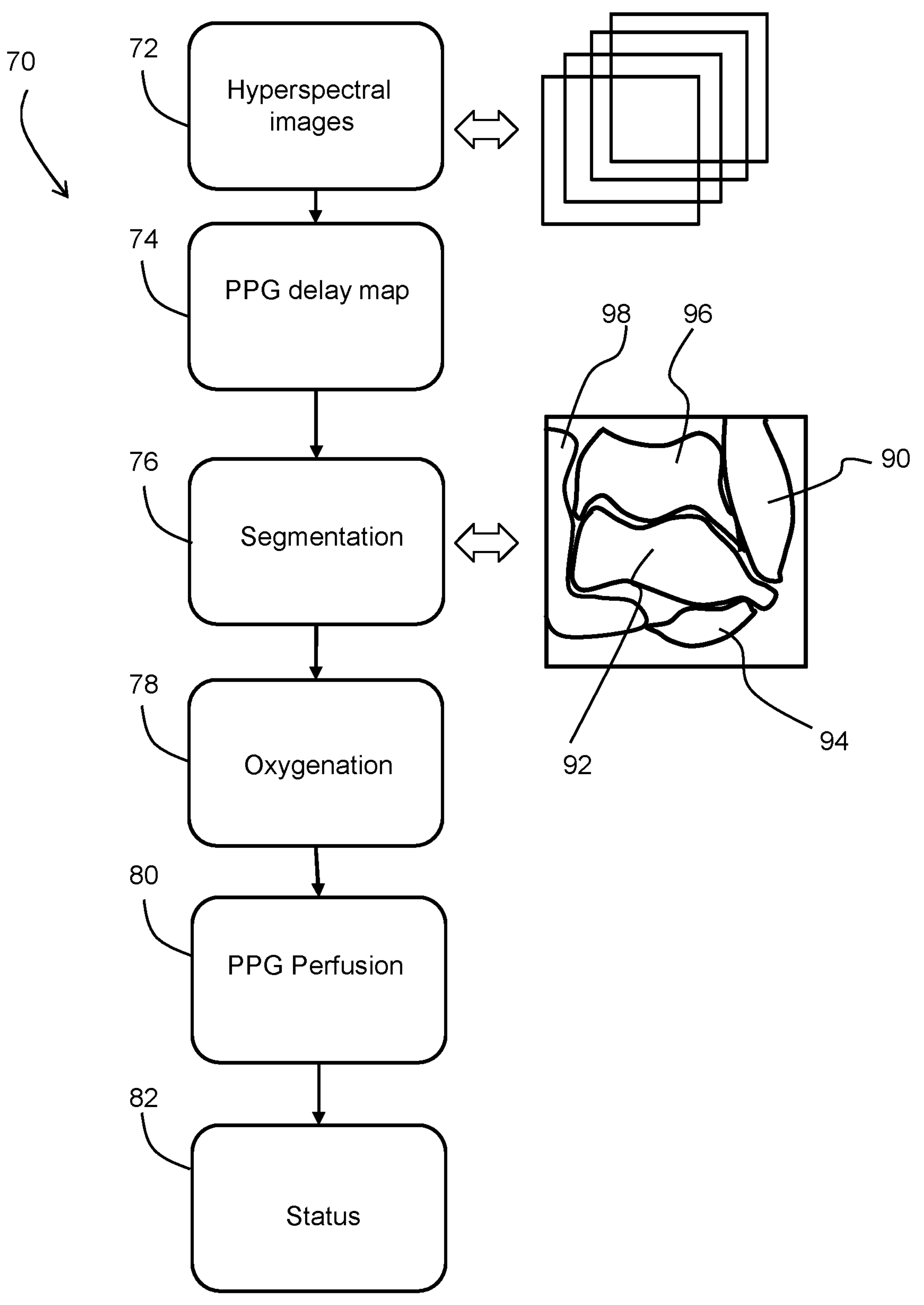
FIG. 7 shows a computer-implemented tissue analysis method.

FIG. 7 shows a computer-implemented tissue analysis method 70.

The method comprises receiving hyperspectral image sensor images in step 72.

Optionally, a PPG delay map is generated in step 74.

In step 76 different tissue types are classified and the hyperspectral images are segmented into one or more regions corresponding to different tissue types.

The image segmentation may be based only on image processing of one or more of the hyperspectral images. However, when a PPG delay map is generated as shown in FIG. 7, the different PPG delays to different regions of the image may also be used (e.g. by a machine learning algorithm) as part of the segmentation of the image into different tissue types.

For example, ranges of PPG delay times, from the PPG delay map, may be used as part of the classification. Different areas may have different global arrival times (relative to a reference or relative to each other) and a delay spread which means they have essentially non-overlapping ranges (e.g. within a number of standard deviations, such as one standard deviation). These differences may thus form part of the machine learning classification.

By way of example, the organs in the abdominal area can be segmented into the spleen 90, colon 92, bladder 94, peritoneum 96 and small intestine 98.

In step 78, a presence or level of tissue oxygenation is estimated for each tissue type. Various approaches are known for extracting blood oxygen saturation from diffuse reflectance spectra and from hyperspectral cameras. For example reference is made to "Stratonnikov A A, Loschenov V B. Evaluation of blood oxygen saturation in vivo from diffuse reflectance spectra. Journal of biomedical optics. 2001 October; 6 (4): 457-67."

The PPG perfusion map is derived in step 80 from PPG amplitude levels at one or more wavelengths of the hyperspectral image sensor.

The estimated tissue oxygenation and PPG perfusion information from the PPG perfusion map are used to derive a tissue perfusion and oxygenation status for each tissue type, and this tissue status is output (e.g. by displaying color-coded images) in step 82.

This invention can be used for assessing the status of the organs during minimally-invasive surgery, in order to reduce the risk of necrosis or even assess the restoration of the correct blood flow of the tissue.

The hyperspectral or other imaging sensor of the system may for example comprise a charged coupled device (CCD) to record images and output the images in analog or digital electronic format or signal. These sensors can comprise a camera such as a hyperspectral camera. Such imaging sensors or cameras are known in the art and available from several vendors.

The system, processor or processor circuit may have an input interface communicatively coupled to the processor, or processor circuit where the input interface is configured to receive images from the imaging sensors to be used by the processor. For example, the images may be received in the analog or digital electronic format or signal.

Functions and methods relating to image processing, data processing and/or output or image generation for output to a user as described herein can be implemented in a general-purpose computer, a processor, processor circuit. Suitable processors or processor circuits include, by way of example, a general-purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors may be made with semiconductor technology as is known in the art.

The system or processor (processor circuit) preferably includes a memory accessible by the processor.

The system or processor (processor circuit) includes an output interface in communicatively coupled to the processor (processor circuit) and configured to output result data and/or images to a user interface or other device for further processing of the result.

The system preferably includes a user interface to be coupled to or coupled to the output interface of the system or processor (processing circuit). Exemplifying user interfaces include a display device having an input for coupling to the output interface and receiving the result data to generate a display of images or the result visible to a user.

Functions and methods related to e.g., image and/or data processing and/or data or image generation described herein can be implemented in a computer program, software, or firmware incorporated in a non-transitory computer-readable storage medium and/or downloadable from a communications network for execution by a general-purpose computer, processor or processor circuit.

A computer program, software or firmware may thus be stored/distributed on a suitable medium an optical storage medium or a solid-state medium supplied together with or as part of other hardware. Examples of non-transitory computer-readable storage media include a read only memory (ROM,) such as electrically programmable ROM (EPROM), electrically erasable programmable ROM (EEPROM or a random access memory (RAM) such as Dynamic RAM (DRAM) or static RAM (SRAM), a register, cache memory, semiconductor memory devices, magnetic media such as internal hard disks and removable disks, magnetooptical media, and optical media such as CD-ROM disks, and digital versatile disks (DVDs). The medium may be a memory of the system accessible by the processor or processor circuit of the system.

Alternatively, or additionally a computer program, software or firmware may be stored and distributed and downloadable from communications network such as wide area network (WAN), local area network (LAN) or Wireless LAN (WLAN), such as the Internet or via other wired or wireless telecommunication systems such as for example 3G, 4G, or 5G networks.

The system may operate at low frame rates, e.g. 20 frames per second or less, and for a short duration such as 20 seconds or less, such as 10 seconds or less. The PPG perfusion may be based on infrared or near-infrared, or other wavelengths such as green. Multiple wavelengths may be used to obtain a better PPG signal.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to". If the term "arrangement" is used in the claims or description, it is noted the term "arrangement" is intended to be equivalent to the term "system", and vice versa.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage.

Any reference signs in the claims should not be construed as limiting the scope.

The invention claimed is:

1. A system for tissue analysis, comprising:

a processor adapted to receive hyperspectral images captured by a hyperspectral image sensor and to process the images to:
 derive a photoplethysmography (PPG) delay map from PPG relative delays between different image regions;
 classify tissue types and segment the hyperspectral images into one or more regions corresponding to different tissue types using the different PPG delays to different regions of the images;
 estimate a presence or level of tissue oxygenation for each tissue type;
 derive a PPG perfusion map from PPG amplitude levels at one or more wavelengths of the hyperspectral image sensor; and
 combine the estimated tissue oxygenation and PPG perfusion information from the PPG perfusion map to derive a tissue perfusion and oxygenation status for each tissue type.

2. The system of claim 1, wherein the processor is adapted to classify the tissue types using a machine learning algorithm.

3. The system of claim 1, wherein the tissue types comprise tissues for different organ types or tissues for different regions of an organ.

4. The system of claim 1, wherein the hyperspectral images comprise a set of 2D images, each at a different wavelength of a set of wavelengths.

5. The system of claim 4, wherein the processor is adapted to estimate the tissue oxygenation using spectral information from hyperspectral images for at least two different wavelengths and to derive the PPG perfusion map from at least one of the 2D images.

6. The system of claim 1, wherein said relative delays comprise a delay relative to a reference PPG signal which is an average delay time period for all image regions for a frame of image data.

7. The system of claim 1, wherein the tissue perfusion and oxygenation status comprises one of:

above normal pulsation and normal oxygenation;
above normal pulsation and below normal oxygenation;
normal pulsation and normal oxygenation;
normal pulsation and below normal oxygenation;
below normal pulsation and normal oxygenation;
below normal pulsation and below normal oxygenation.

8. The system of claim 1, further comprising a hyperspectral image sensor for capturing the hyperspectral images.

9. The system of claim 1, wherein the processor is further adapted to obtain a standard level of perfusion at homeostasis for each classified tissue type, for comparison with the derived tissue perfusion status.

10. A computer-implemented tissue analysis method, comprising:

receiving hyperspectral image sensor images;
deriving a PPG delay map from PPG relative delays between different image regions;
classifying tissue types and segmenting the hyperspectral images into one or more regions corresponding to different tissue types using the different PPG delays to different regions of the images;
estimating a presence or level of tissue oxygenation for each tissue type;

deriving a PPG perfusion map from PPG amplitude levels at one or more wavelengths of the hyperspectral image sensor; and combining the estimated tissue oxygenation and PPG perfusion information from the PPG perfusion map to derive a tissue perfusion and oxygenation status for each tissue type.

11. The method of claim 10, wherein the tissue types comprise tissues for different organ types or tissues for different regions of an organ.

12. The method of claim 10, wherein the hyperspectral images comprise a set of 2D images, each at a different wavelength of a set of wavelength and wherein the method comprises:

estimating the tissue oxygenation using spectral information from hyperspectral images for at least two different wavelengths; and deriving the PPG perfusion map from at least one of the 2D images.

13. The method of claim 10, comprising obtaining a standard level of perfusion at homeostasis for each classified tissue type, for comparison with the derived tissue perfusion status.

14. A non-transitory computer-readable medium storing instructions that, when executed by a processor, causes the processor to perform a method comprising:

receiving hyperspectral images captured by a hyperspectral image sensor:

deriving a photoplethysmography (PPG) delay map from PPG relative delays between different image regions;

classifying tissue types and segment the hyperspectral images into one or more regions corresponding to different tissue types using the different PPG delays to different regions of the images;

estimating a presence or level of tissue oxygenation for each tissue type;

deriving a PPG perfusion map from PPG amplitude levels at one or more wavelengths of the hyperspectral image sensor; and combining the estimated tissue oxygenation and PPG perfusion information from the PPG perfusion map to derive a tissue perfusion and oxygenation status for each tissue type.

15. The non-transitory computer-readable medium of claim 14, wherein the hyperspectral images comprise a set of 2D images, each at a different wavelength of a set of wavelength, and wherein the method performed by the processor comprises:

estimating the tissue oxygenation using spectral information from hyperspectral images for at least two different wavelengths; and deriving the PPG perfusion map from at least one of the 2D images.

* * * * *